US011141383B1

(12) United States Patent
Ahmed et al.

(10) Patent No.: US 11,141,383 B1
(45) Date of Patent: Oct. 12, 2021

(54) DRUG LOADED FLEXIBLE CHITOPLEXES NANOPARTICLES

(71) Applicant: King Abdulaziz University, Jeddah (SA)

(72) Inventors: Tarek A. Ahmed, Jeddah (SA); Abdelsattar M. Omar, Jeddah (SA)

(73) Assignee: KING ABDULAZIZ UNIVERSITY, Jeddah (SA)

( * ) Notice: Subject to any disclaimer, the term of this patent is extended or adjusted under 35 U.S.C. 154(b) by 0 days.

(21) Appl. No.: 16/910,732

(22) Filed: Jun. 24, 2020

(51) Int. Cl.
| | | |
|---|---|---|
| *A61K 9/51* | (2006.01) | |
| *A61K 31/505* | (2006.01) | |
| *A61K 9/127* | (2006.01) | |
| *A61K 31/40* | (2006.01) | |
| *A61K 31/44* | (2006.01) | |
| *A61K 31/366* | (2006.01) | |
| *A61K 31/47* | (2006.01) | |
| *A61K 31/22* | (2006.01) | |
| *A61K 31/405* | (2006.01) | |

(52) U.S. Cl.
CPC ............ *A61K 9/5161* (2013.01); *A61K 9/127* (2013.01); *A61K 9/1271* (2013.01); *A61K 9/5123* (2013.01); *A61K 31/22* (2013.01); *A61K 31/366* (2013.01); *A61K 31/40* (2013.01); *A61K 31/405* (2013.01); *A61K 31/44* (2013.01); *A61K 31/47* (2013.01); *A61K 31/505* (2013.01); *Y10S 977/773* (2013.01); *Y10S 977/906* (2013.01); *Y10S 977/907* (2013.01)

(58) Field of Classification Search
None
See application file for complete search history.

(56) References Cited

U.S. PATENT DOCUMENTS

| | | | | |
|---|---|---|---|---|
| 2012/0225487 A1* | 9/2012 | Weber | ................... | G01N 33/50 436/93 |
| 2014/0088126 A1* | 3/2014 | Scallen | ................... | A61P 33/00 514/275 |
| 2017/0056404 A1* | 3/2017 | Vali | ...................... | A61K 31/155 |

OTHER PUBLICATIONS

Mohammed O. Alshraim, Sibghatullah Sangi, Gamaleldin I. Harisa, Abdullah H. Alomrani, Osman Yusuf, and Mohamed M. Badran. "Chitosan-Coated Flexible Liposomes Magnify the Anticancer Activity and Bioavailability of Docetaxel: Impact on Composition." Molecules 2019, 24, 250, pp. 1-14. (Year: 2019).*

Chunyang Wang, et al. "Rosuvastatin, Identified From a Zebrafish Chemical Genetic Screen for Antiangiogenic Compounds, Suppresses the Growth of Prostate Cancer." European Urology, vol. 58, 2010, pp. 418-426. (Year: 2010).*

U Laufs et al. "Rosuvastatin, a new HMG-CoA reductase inhibitor, upregulates endothelial nitric oxide synthase and protects from ischemic stroke in mice." Brain Research, vol. 942, 2002, pp. 23-30. (Year: 2002).*

(Continued)

Primary Examiner — Isaac Shomer
(74) Attorney, Agent, or Firm — W&C IP

(57) ABSTRACT

Chitosan-coated, flexible lipid-based nanoparticles are provided. The nanoparticles ("chitoplexes") comprise an interior comprising a mixture of a phospholipid, an edge activator, a charge inducing agent, and a statin; and an exterior chitosan coating which encapsulates the interior mixture. The chitoplexes exhibit enhanced bioavailability with respect to delivering the statins encapsulated therein to a subject, for example, for the treatment of cancer.

9 Claims, 6 Drawing Sheets
(4 of 6 Drawing Sheet(s) Filed in Color)

(56) References Cited

OTHER PUBLICATIONS

A Alomrani et al. "The use of chitosan-coated flexible liposomes as a remarkable carrier to enhance the antitumor efficacy of 5-fluorouracil against colorectal cancer." Saudi Pharmaceutical Journal, vol. 27 (2019), pp. 603-611, available online Mar. 1, 2019. (Year: 2019).*
Tarek A. Ahmed. "Development of rosuvastatin flexible lipid-based nanoparticles: promising nanocarriers for improving intestinal cells cytotoxicity." BMC Pharmacology and Toxicology, vol. 21:14, 2020, pp. 1-12. (Year: 2020).*
Denise M Boudreau, Onchee Yu, Jeanene Johnson. "Statin use and cancer risk: a comprehensive review." Expert Opinion in Drug Safety, (2010) 9(4), pp. 603-621. (Year: 2010).*
Mohsen M. Mady, Mirhane M. Darwish. "Effect of chitosan coating on the characteristics of DPPC liposomes." Cairo University Journal of Advanced Research, vol. 1, 2010, pp. 187-191. (Year: 2010).*
Naveena B. Janakiram et al. "Potentiating NK cell activity by combination of Rosuvastatin and Difluoromethylornithine for effective chemopreventive efficacy." Scientific Reports, 6:37046 | DOI: 10.1038/srep37046, 2016, pp. 1-13. (Year: 2016).*
Senem Aykul, Erik Martinez-Hackert. "Determination of half-maximal inhibitory concentration using biosensor-based protein interaction analysis." Analytical Biochemistry 508 (2016), pp. 97-103. (Year: 2016).*
Heather Eng et al. "The Antimicrobial Agent Fusidic Acid Inhibits Organic Anion Transporting Polypeptide-Mediated Hepatic Clearance and May Potentiate Statin-Induced Myopathy." Drug Metabolism and Disposition, vol. 44, May 2016, pp. 692-699. (Year: 2016).*
Malgorzata Maj, Rafal Czajkowski, Barbara Zegarska, Bogna Kowaliszyn, Marta Pokrywczynska, Tomasz Drewa. "Antiproliferative and cytotoxic activity of rosuvastatin against melanoma cells." Advances in Dermatology and Allergology, vol. 4, Aug. 2016, pp. 257-262. (Year: 2016).*
Mukundkumar Rameshbhai Hirpara et al. "Long circulating PEGylated-chitosan nanoparticles of rosuvastatincalcium: Development and in vitro and in vivo evaluations." International Journal of Biological Macromolecules 107 (2018), pp. 2190-2200. (Year: 2018).*
Pal Tapas Kumar, Jayita Mishra and Abhishekh Podder. "Design, Fabrication and Evaluation of Rosuvastatin Pharmacosome—A Novel Sustained Release Drug Delivery System." European Journal of Pharmaceutical and Medical Research, vol. 3(4), 2016, pp. 332-350. (Year: 2016).*

* cited by examiner

DRUG LOADED FLEXIBLE CHITOPLEXES NANOPARTICLES

BACKGROUND OF THE INVENTION

Field of the Invention

The invention generally relates to improved nano-vesicles for administering statins. In particular, the invention provides flexible liposomes coated with chitosan (chitoplexes), to deliver statins with increased bioavailability.

Description of Related Art

Rosuvastatin (RSV), a member of the statins, is used to prevent cardiovascular disorders by decreasing the low-density lipoprotein (LDL) cholesterol. It is the most effective hypolipidemic agent of the statin group and has been designated a "super-statin". Similar to other statins, the mechanism of action of RSV is attributed to competitive inhibition of the enzyme 3-hydroxy-3-methyl-glutaryl-CoA (HMG-CoA) reductase. RSV has a low water solubility and exhibits only limited solubility in the gastrointestinal fluids. The drug is subjected to extensive first pass metabolism after oral administration. Accordingly, the oral bioavailability of RSV is approximately only 20%. The maximum RSV plasma concentration is reached in about 3 to 5 hours. The drug is 88% bound to plasma protein, mainly to serum albumin. It is probable that about 25% of the orally administered dose is absorbed. RSV is mainly metabolized by the liver enzyme CYP2C9 and is 90% excreted in feces, the drug elimination half-life being nearly 19 hours.

Different pharmaceutical formulation strategies have been used to enhance the bioavailability of drugs that suffer from poor aqueous solubility, such as RSV. These include size reduction, the use of cosolvents and surfactants, solid dispersion and inclusion complexation techniques, salt formation and prodrug approaches. Moreover, formation of colloidal drug delivery systems such as solid lipid nanoparticles (NPs), polymeric based NPs, lipid based NPs, microemulsion formations and self-microemulsifying drug delivery systems have been reported.

Flexible liposomes have been denominated "Transfersomes" and these NPs constitute a class of lipid-based NPs which include phospholipid(s) and a single chain surfactant. The presence of surfactant (edge activator) promotes flexibility of these NPs by reducing the rigidity of the phospholipid bilayer and so render these nanocarriers ultra-deformable vesicles. Due to their successful delivery of a wide variety of pharmacologically active agents, these ultra-deformable NPs have attracted much research interest.

SUMMARY OF THE INVENTION

Compositions and methods for the improved bioavailability of statins are provided. In exemplary aspects, the compositions are flexible lipid-based nanoparticles comprising, at an interior, a phospholipid, an edge activator, a charge inducing agent, and a statin. The interior mixture is encapsulated by a coating of chitosan. Due to their ability to provide enhanced bioavailability of statins, in further exemplary aspects, the chitoplexes are utilized in methods of treating cancer. The "chitoplexes" advantageously exhibit a biphasic drug release profile with a lower initial and more extended drug release pattern when compared to corresponding liposomal NPs. In addition, they also exhibit smaller $IC_{50}$ values and superior anticancer activity in a time- and dose-dependent manner, compared to corresponding liposomal NPs.

It is an object of this invention to provide a flexible chitosan-coated liposomes formulation, comprising an interior comprising: at least one phospholipid, at least one edge activator, at least one charge inducing agent, and at least one statin; and an exterior coating of chitosan that encapsulates the interior. In some aspects, the at least one phospholipid is selected from the group consisting of: phosphatidylcholine, phosphatidylethanolamine, phosphatidylserine, phosphatidic acid, phosphatidylinositol and phosphatidylglycerol. In further aspects, the at least one edge activator is selected from the group consisting of polysorbate-20, polysorbate-40, polysorbate-60, and polysorbate-80. In additional aspects, the at least one charge inducing agent is selected from the group consisting of: dicetyl phosphate, phosphatidic acid, stearylamine and cetylpyridinium chloride. And in yet other aspects, the at least one statin is selected from the group consisting of: atorvastatin, cerivastatin, fluvastatin, lovastatin, pitavastatin, pravastatin, rosuvastatin, simvastatin. In additional aspect, the at least one phospholipid is present in an amount of from 0.5 to 5.0% (w/v); the at least one edge activator is present in an amount of from 0.5 to about 5.0% (w/v); the at least one charge inducing agent is present in an amount of 10 to 20% w/w; the at least one statin is present in an amount of 0.01 to about 0.5% (w/v), and the chitosan is present in an amount of 0.2-0.6% (w/v). In further aspects, the at least one phospholipid is phosphatidylcholine; and/or the at least one edge activator is polysorbate-80 (IUPAC 24243,5-bis(2-hydroxyethoxy)oxolan-2-yl]-2-(2-hydroxyethoxy)ethoxy]ethyl (E)-octadec-9-enoate) and/or the at least one charge inducing agent is dicetyl phosphate; and/or the at least one statin is rosuvastatin. In further aspects, a diameter of the flexible chitosan-coated nanoparticle ranges from 100 to 600 nm. In certain aspects, the exterior coating of chitosan has a thickness ranging from 15 to 275 nm, and in further aspect, the thickness is approximately 100.75 nm.

Also provided is a pharmaceutical composition comprising the flexible chitosan-coated liposomes described in the preceding paragraph, and a carrier. In some aspects, the carrier is a liquid and the pharmaceutical composition is formulated for injection; or the carrier is a solid or gel and the pharmaceutical composition is formulated i) as a tablet, capsule or powder for oral administration or ii) as a tablet, capsule or powder for dissolution in a liquid; or the carrier is a gelatin capsule.

Also provided are methods of treating cancer in a subject in need thereof, comprising administering to the subject a composition comprising a plurality of flexible chitosan-coated liposomes as described above. In some aspects, the cancer is selected from the group consisting of colorectal cancer, thyroid cancer, hepatic cancer, breast cancer, cervical, cancer prostate cancer and melanoma.

Further aspects provide methods of inhibiting the mevalonate pathway in a subject in need thereof, comprising administering to the subject a composition comprising a plurality of flexible chitosan-coated liposomes as described above and claimed herein.

Other features and advantages of the present invention will be set forth in the description of invention that follows, and in part will be apparent from the description or may be learned by practice of the invention. The invention will be realized and attained by the compositions and methods particularly pointed out in the written description and claims hereof.

Figure 1:
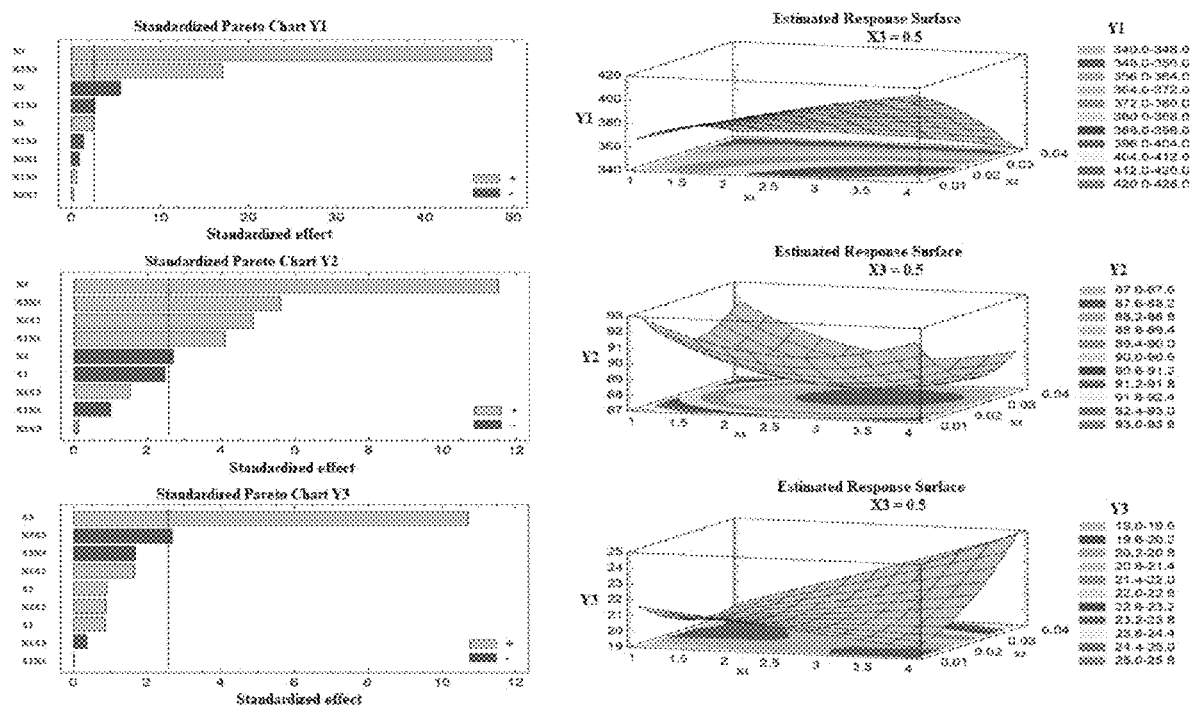
FIG. 1. Standardized Pareto charts and response surface plots for the effect of the studied factors on $Y_1$-$Y_3$. Abbreviations: $X_1$, Drug to phospholipid; $X_2$, Surfactant concentration; $X_3$, Coating solution concentration; $Y_1$, Particle size (nm); $Y_2$, Entrapment efficiency (%); $Y_3$, Zeta potential (mV); $X_1X_2$, $X_1X_3$, and $X_2X_3$ are the interaction effects of the studied factors; $X_1X_1$, $X_2X_2$ and $X_3X_3$ are the quadratic effects of factors.

The patent or application file contains at least one drawing executed in color. Copies of this patent or patent application publication with color drawings will be provided by the Office upon request and payment of the necessary fee.

DETAILED DESCRIPTION

The disclosure describes flexible lipid-based nanoparticles ("chitoplexes") comprising a phospholipid, an edge activator, a charge inducing agent, and a statin in the interior of the nanoparticles, and an exterior coating of chitosan that encapsulates the interior mixture. The chitoplexes are used to deliver statins in order to treat a variety of diseases. In particular, due to their extended release profiles and excellent $IC_{50}$ values, they are suitable for the treatment of cancers such as colorectal cancer, where extended drug release patterns are advantageous. An exemplary phospholipid is L-α phosphatidylcholine, an exemplary edge activator (surfactant) is TWEEN 80®, an exemplary charge inducing agent is dicetyl phosphate, and an exemplary statin is rosuvastatin.

Phospholipid

At least one phospholipid is present in the chitoplexes. Examples of phospholipids that may be used include but are not limited to: phosphatidylcholine, phosphatidylethanolamine, phosphatidylserine, phosphatidic acid, phosphatidylinositol and phosphatidylglycerol. In some aspects, the phospholipid is phosphatidylcholine e.g. L-α phosphatidylcholine. The at least one phospholipid is generally present in an amount ranging from about 0.5 to about 5.0% (w/v) of the total formulation volume, such as from about 0.6 to about 4.0% w/v or about 0.7 to about 3.5% w/v). In some aspects, the phospholipid is present in an amount from 0.775 to 3.1% (w/v) of the total formulation volume.

Edge Activator (Surfactant)

One or more edge activators are present in the compositions, examples of which include but are not limited to: various nonionic surfactants and emulsifiers such as polysorbates, e.g. polyethylene sorbitol ester polysorbate-type nonionic surfactants such as polysorbate-20, polysorbate-40, polysorbate-60, and polysorbate-80. Commercially available polysorbates include the "Tweens", condensates of sorbitol fatty acid ester and ethylene oxide, common commercial brand names of which include Scattics, ALKEST® TW 20, and TWEEN 20®. In some aspects, the edge activator is polysorbate-80, the generic name for which is polyoxyethylene (20) sorbitan monooleate, and which is commercially available as TWEEN 80®. Other polysorbates are generally commercially available under similar naming conventions, e.g. TWEEN 20®, TWEEN 40®, TWEEN 60®, etc.

The at least one edge activator is generally present in the formulations in an amount ranging from about 0.005 to 0.05% w/v, e.g. about 0.005, 0.01, 0.015, 0.02, 0.025, 0.03, 0.035, 0.04, 0.045 or 0.05% (w/v) of the total formulation volume; and is generally in the range of from about 0.01-0.04% (w/v) based on the total formulation volume.

Charge Inducing Agent

The compositions include at least one charge inducing agent, examples of which include but are not limited to: dicetyl phosphate, phosphatidic acid, stearylamine and cetylpyridinium chloride. In some aspects, the charge inducing agent is dicetyl phosphate.

The charge inducing agent is generally present in the compositions in an amount (concentration) of from about 5-20% w/w of the total lipid (total lipid is the weight of phospholipid only (L-α phosphatidylcholine)) e.g. about 5, 10, 15, or 20% w/w. In some aspects, the amount is 15% w/w of the total lipid.

Statin

The drug that is contained within in the flexible liposomes described herein is typically a statin. Examples of suitable statins include but are not limited to atorvastatin, cerivastatin, fluvastatin, lovastatin, pitavastatin, pravastatin, rosuvastatin, simvastatin, and mevastatin, including isomers and pharmaceutically acceptable salts and prodrugs thereof. For example, the statin may be rosuvastatin calcium.

Statins can also be present in the formulations in combinations of more than one form; that means that a statin may be present as salt (including calcium, sodium and potassium salts), acid (e.g. carboxylic acid) or in neutral, closed lactone ring form. The desired combination of statins depends upon the proposed end user, the solubility of the combination and the end-goal of the treatment.

The at least one statin is generally present in an amount of from about 0.01 to about 0.5%, e.g. about 0.01, 0.05, 0.075, 0.10, 0.15, 0.20, 0.25, 0.3, 0.35, 0.4, 0.45 or 0.5% (w/v). In some aspects, the amount is about 0.1% (w/v).

Chitosan

Chitosan is used to create a coating on the flexible nanoparticles. Chitosan is a linear polysaccharide composed of randomly distributed β-(1→4)-linked D-glucosamine (deacetylated unit) and N-acetyl-D-glucosamine (acetylated unit). It is made by treating the chitin shells of shrimp and other crustaceans with an alkaline substance, such as sodium hydroxide. Commercial sources of chitosan are well-known.

The amount of chitosan in a coated nanoparticle as described herein is generally in the range of from about 0.1 to about 1.0% (w/v) of the total formulation volume, for example, about 0.2-0.6% (w/v) of the total formulation volume.

The thickness of the coating of chitosan generally ranges from about 15.0 nm (such as about 15.46 nm) to about 275.0 nm (such as about 272.01 nm), e.g. about 15, 25, 50, 75, 100, 125, 150, 175, 200, 225, 250 or 275 inclusive, including all digits to two decimal places in between. In some aspects, the thickness of the coating of chitosan in optimized chitoplexes is about 100 nm, such as about 100.75 nm.

Characteristics of the Chitoplexes

The chitoplexes generally have a size (diameter) ranging from about 100 to about 600 nm, e.g. is about 100, 150, 200, 250, 300, 350, 400, 450, 500, 550 or 600 nm. In some aspects, the size ranges from about 112.19±2.90-554.33±11.06 nm.

The Poly dispersity index PDI of the chitoplexes generally ranges from about 0.2 to 0.6, e.g. is about 0.2, 0.25, 0.3, 0.35, 0.4, 0.45, 0.5, 0.55 or 0.6. In some aspects, the PDI ranges from about 0.258±0.023-0.581±0.051.

The Entrapment efficiency (EE) of the chitoplexes generally ranges from about 80 to 100%, e.g. is about 80, 85, 90, 95 or 100%. In some aspects, the EE ranges from about 84.78±3.09-94.59±1.62%.

The zeta potential value, which indicates surface charge of the particles, generally ranges from about −15 to about +30, e.g. is about −15, −10, −5, 0, 5, 10, 15, 20, 25 or 30 mV. In some aspects, the zeta potential was in the range of (−10.07±1.26)-(+28.87±1.39) mV.

The flexibility value of the chitoplexes generally ranges from about 35 to 45%, e.g. is about 35, 36, 40, 42, 42, 43, 44 or 45%. In some aspects, the value is 40.16%. Flexibility of the nanoparticles refers to the change in the nanoparticle size after extrusion under reduced pressure across a membrane filter of a specific pore size.

Figure 6:
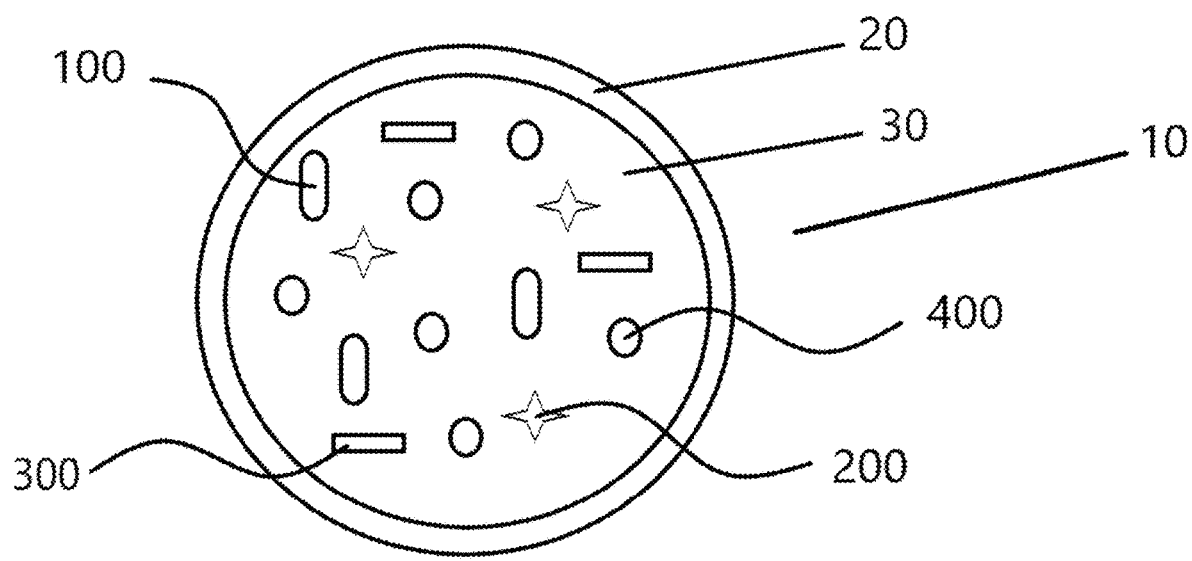
FIG. 6. Schematic representation of a chitoplexes nano-formulation.

FIG. 6 shows a schematic representation of a chitoplexes formulation. What is shown is chitoplexes formulation 10 having coating 20 and interior 30. Phospholipids 100, charge inducing agents 200, edge activators 300 and statins 400 are shown intermixed within interior 30, i.e. they make up interior 30, or interior 30 is formed from and comprises phospholipids 100, charge inducing agents 200, edge activators 300 and statins 400. The sizes, distributions, ratios and amounts are not to scale in FIG. 6 and are representational/schematic only.

Diseases that are Prevented and/or Treated

The chitoplexes described herein can be used to treat any disease that is amenable to treatment with a statin or statins. Statins are used to lower cholesterol levels in the blood and as such uses include preventing and/or treating cardiovascular diseases (CVDs), including coronary heart disease, heart attack, stroke, transient ischemic attack (TIA), and peripheral vascular disease. Statins have additional benefits beyond lowering cholesterol levels such as improved endothelial function, enhanced stability of atherosclerotic plaques, reduced inflammation and damage to cells through oxidation (oxidative stress), lowering C reactive protein and preventing platelet aggregation (thereby reducing the risk of thrombus), and their use may help to treat/prevent diseases such as multiple sclerosis (MS), inflammatory bowel diseases (IBDs), rheumatoid arthritis (RA), systemic lupus erythematosus (SLE), chronic obstructive pulmonary disease (COPD), cancer, strokes, Parkinson's and Alzheimer's diseases, bacterial infections, HIV, and various autoimmune and chronic inflammatory diseases.

Statins may also be used in the treatment of cancer and the chitoplexes described herein are particularly useful in this respect to the enhanced bioavailability they display. Types of cancer that may be treated using the chitoplexes include but are not limited to: cancers of the colon, breast, and prostate; osteosarcoma, chorioademoma destruens, choriocarcinoma, hydatidiform mole, acute lymphocytic leukaemia, acute non-lymphocytic leukaemia, large cell lymphoma, high-grade lymphoma, non-Hodgkin's lymphoma, lymphosarcoma, Burkitt's lymphoma, cutaneous T cell lymphoma, pleural mesothelioma, breast cancer, ovarian cancer, squamous head tumour, squamous neck tumour, small cell lung carcinoma, thyroid cancer, prostate cancer, gastric cancer, hepatic cancer, cervical cancer, melanoma and urinary bladder cancer. In some aspects, the cancer is colon cancer. Metastases, relapses and recurrences are also encompassed.

Administration and Dosing

The chitoplexes described herein are generally delivered (administered) in a pharmaceutical composition. Such pharmaceutical compositions generally comprise at least one chitoplexes formulation, wherein each formulation contains chitoplexes which include the same type of statin. However, combinations of two or more different types of chitoplexes formulation are also encompassed, so that more than one statin is delivered in the pharmaceutical composition. It is noted that a single type of chitoplexes formulation may also include more than one type of statin.

The compositions generally include the chitoplexes and a pharmacologically suitable (physiologically compatible) carrier, which may be liquid, solid or semi-solid. If the carrier is a liquid, the chitoplexes can be e.g. suspended in the liquid, and generally the liquid will be of a type in which the chitoplexes are not soluble or are only sparingly soluble. Exceptions include when the chitoplexes are mixed with the liquid carrier immediately before administration so that there is insufficient time for the chitosan coating to dissolve. Liquid carriers are aqueous in nature. It is noted that oil based liquid is not acceptable, since the outer surface of the chitoplexes is phospholipid. Accordingly, chitoplexes could dissolve in an oily liquid, an effect that will disrupt the prepared vesicles.

Solid and semi-solid carriers may also be employed. The chitoplexes may be compressed into e.g. the form of a solid tablet, pill, powder or capsule in which they are surrounded by a solid matrix or may be suspended or embedded e.g. in a gel, hydrogel or viscous liquid. Alternatively, the chitoplexes may be present within an otherwise empty solid but dissolvable capsule such as within a gelatin capsule.

In some aspect, the carrier is a solid or gel and the pharmaceutical composition is formulated i) as a tablet, capsule or powder for oral administration or ii) as a tablet, capsule or powder for dissolution in a liquid. For example, powder forms may be provided which are added to a liquid immediately prior to injection.

Various pharmaceutically acceptable excipients that are compatible with the chitoplexes are used to form the compositions. Suitable excipients include, for example, water, saline, dextrose, glycerol, and the like, or combinations thereof. In addition, the composition may contain minor amounts of auxiliary substances such as wetting or emulsifying agents, pH buffering agents, preservatives, and the like. If it is desired to administer an oral form of the composition, various thickeners, flavorings, diluents, emulsifiers, dispersing aids or binders and the like are added. The composition of the present invention may contain any such additional ingredients so as to provide the composition in a form suitable for administration. The final amount of a statin in the formulations varies but is generally from about 1-99%. Still other suitable formulations for use in the present invention are found, for example in Remington's Pharmaceutical Sciences, 22nd ed. (2012; eds. Allen, Adejarem Desselle and Felton).

The chitoplexes or compositions comprising the chitoplexes may be administered in vivo by any suitable route including but not limited to: parenteral (e.g. intravenously, intratumorally or as an implant), oral (e.g. as a pill, capsule, liquid, etc.), vaginal or rectal (as a suppository, pessaries, creams, ointment, gels, foams or inserts) etc. In preferred embodiments, the mode of administration is the oral or intravenous route. In addition, the compositions may be administered in conjunction with other treatment modalities such as substances that boost the immune system, various chemotherapeutic agents (e.g. other anti-neoplastic agents), other antibiotic agents, resection surgery, radiation therapy, and the like.

The amount of chitoplexes formulation composition that is administered varies depending on e.g. the type of statin, the type of cancer being treated, the medical condition of the subject (e.g. age, gender, overall health, etc.), as well as the weight of the subject. The final dose of statin per day, for treatment of hyperlipidemia, is generally in the range of from about 2.5 to about 80 mg, e.g. about 2.5, 5, 10, 15, 20, 25, 30, 35, 40, 45, 50, 55, 60, 65, 709, 75 or 80 mg per day, depending on the statin. For pitavastatin, the dose is generally lower such as in the range of 1-4 mg (e.g. 1, 2, 3, or 4 mg) per day, and for rosuvastatin, the dose generally ranges from about 5-40 mg per day. Higher doses of statins, which are not used in hypercholesterolemia therapy in humans, may be required or used to achieve antitumor activity. Those of skill in the art such as physicians are best positioned to determine the dose that should be used.

Methods of Making the Chitoplexes

The chitoplexes may be made by any suitable method, examples of which include the mechanical dispersion methods (such as; lipid film hydration method, micro-emulsification method and membrane extrusion method), solvent dispersion methods (such as; organic solvent injection method, double emulsion method and reverse phase evaporation method) and detergent removal methods. In some aspects, a lipid film hydration technique may be used to prepare the NP formulations. The statin, phospholipid, edge activator and charge inducing agent are dispersed in an organic solvent (e.g. methanol, ethanol, chloroform, and ether) in a suitable flask and subjected to sonication until a homogenous dispersion is obtained. The solvent is evaporated (e.g. under elevated temperature, e.g. 40-60° C., such as about 50° C., and reduced pressure) with continuous rotation to form a lipid film deposited inside the flask. The film is dried e.g. under vacuum. Hydration medium is added (e.g. phosphate or other suitable buffer, typically at or near physiological pH, such as about pH 7.0) with shaking and sonication to obtain a dispersion of flexible liposomal NPs.

The flexible liposomal NPs are coated with chitosan as follows: chitosan is dissolved in a suitable solvent, e.g. acetic acid. The chitosan solution is added dropwise to an equal volume of the prepared flexible liposomal dispersion with stirring (e.g. at about 1000 to 1400 rpm, such as 1200 rpm for e.g. 1-3 hours, such as about 2 h at room temperature) and left in the cold (e.g. refrigerated for several hours or overnight) for complete curing.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

Example

Abbreviations

RSV; Rosuvastatin, NPs; nanoparticles, EE; entrapment efficiency, PDI; polydispersity index, IC50; The half maximum inhibitory concentrations, LDL; low-density lipoprotein, HMG-CoA; 3-hydroxy-3-methyl-glutaryl-CoA; DCP; Dicetyl phosphate; $X_1$, Drug to phospholipid; $X_2$, Surfactant concentration; $X_3$, Coating solution concentration; $Y_1$, Particle size (nm); $Y_2$, Entrapment efficiency (%); $Y_3$, Zeta potential (mV); $X_1X_2$, $X_1X_3$, and $X_2X_3$ are the interaction effects of the studied factors; $X_1X_1$, $X_2X_2$ and $X_3X_3$ are the quadratic effects of factors, MTT; 3-(4,5-dimethylthiazol-2-yl)2,5-diphenyl tetrazolium bromide, ANOVA, analysis of variance, FT-IR; Fourier transforms infrared. TEM; transmission electron microscopy.

Materials and Methods
Materials

Rosuvastatin (RSV) was obtained as a gift from the Saudi Arabian Japanese Pharmaceuticals Co. Ltd (SAJA) (Jeddah, KSA). Dicetyl phosphate (DCP) and methanol were purchased from Fisher Scientific (Pittsburgh, Pa., USA). TWEEN® 80, low molecular weight chitosan and glacial acetic acid were procured from Sigma-Aldrich (St. Louis, Mich., USA). L-α phosphatidylcholine (95%) (soy), molecular weight=775.037 (average based on fatty acid distribution in product) was purchased from Avanti® polar lipids, INC. (Alabaster, Ala., USA). All other materials used were of analytical grade.

Box-Behnken Experimental Design

StatGraphics Centurion XV version 15.2.05 software, StatPoint Technologies, Inc., (Warrenton, Va., USA) was employed to study the effect of three independent factors affecting the development of RSV chitosan-coated flexible lipid-based nanocarrier (chitoplexes). The drug to phospholipid molar ratio ($X_1$), the surfactant (edge activator) concentration ($X_2$) and the chitosan coating solution concentration ($X_3$) were studied for their effect on vesicle size ($Y_1$), entrapment efficiency ($Y_2$) and zeta potential ($Y_3$). Fifteen formulations were proposed, and their composition is illustrated in Table 1. The studied independent factors were namely; $X_1$, $X_2$ and $X_3$ were used at 1:1-1:4 drug to phospholipid molar ratios, 0.01-0.04% (w/v) based on the total formulation volume and 0.2-0.6% (w/v), respectively. The goal was to minimize $Y_1$ and maximize both $Y_2$ and $Y_3$.

ture was subjected to sonication using Ultrawave Ltd., CF3 2EY water bath sonicator (Cardif, UK) until homogenous dispersion was obtained. The organic solvent, methanol, was evaporated at a temperature of 50° C. under reduced pressure and continuous rotation using Buchi Rotavapor R-200, Buchi labortechink AG, CH-9230 (Flawi, Switzerland). The obtained lipid film deposited inside the flask wall was kept for 24 h in a vacuum oven of Thermo Fisher Scientific, model 6505 (Oakwood Village, Ohio, USA) to ensure complete evaporation of methanol. The hydration medium, 50 mL of phosphate buffer pH 7, was added to the flask that was kept shaking in the rotavapor for 30 minutes at 50° C. The obtained flexible liposomal dispersion was subjected to probe sonication using Sonics Vibra cell, VCX 750; Sonics & Materials, Inc. (Newtown, Conn., USA) for 10 minutes at an amplitude of 60%.

For the coating step, three chitosan solutions (0.4, 0.8 and 1.2% w/v) were prepared by dissolving the calculated amount of chitosan in 0.5% v/v acetic acid solution. According to the formulation composition, 50 mL of the specified chitosan solution was added dropwise to an equal volume of the prepared flexible liposomal dispersion over a magnetic stirrer at 1200 rpm for 2 h at room temperature. The prepared chitosan-coated flexible liposomal NPs (chitoplexes nano-formulation) of 0.2, 0.4 or 0.6% w/v chitosan were left over night in the refrigerator for complete curing of the NPs.

A specified volume of the obtained flexible liposomal NPs was separated and characterized, as described in the following section, to compare their features with the corresponding chitoplexes nano-formulation.

Characterization of the Flexible Lipid-Based Nanoparticles
Particle Size Distribution and Zeta Potential The particle size, polydispersity index (PDI) and zeta potential for the prepared fifteen NP formulations were determined (n=3) using Malvern Zetasizer Nano ZSP, Malvern Panalytical Ltd (Malvern, United Kingdom).

TABLE 1

Composition of rosuvastatin chitoplexes nanoparticle formulations and the obtained values for the studied responses

| Run | $X_1$ (MR) | $X_2$ (%) | $X_3$ (%) | $Y_1$ Size (nm) | $Y_1$ PDI | $Y_2$ (%) | $Y_3$ (mV) |
|---|---|---|---|---|---|---|---|
| 1 | 1.0 | 0.01 | 0.4 | 239.48 ± 5.33 | 0.344 ± 0.065 | 90.88 ± 1.65 | 12.66 ± 1.58 |
| 2 | 4.0 | 0.04 | 0.4 | 225.27 ± 6.59 | 0.425 ± 0.095 | 86.94 ± 4.94 | 18.10 ± 3.38 |
| 3 | 2.5 | 0.04 | 0.2 | 112.19 ± 2.90 | 0.288 ± 0.009 | 85.14 ± 5.04 | −1.83 ± 0.55 |
| 4 | 2.5 | 0.01 | 0.6 | 554.33 ± 11.06 | 0.573 ± 0.045 | 94.59 ± 1.62 | 26.74 ± 0.26 |
| 5 | 2.5 | 0.04 | 0.6 | 507.40 ± 18.14 | 0.581 ± 0.051 | 91.97 ± 4.89 | 26.07 ± 1.90 |
| 6 | 4.0 | 0.01 | 0.4 | 295.40 ± 5.11 | 0.258 ± 0.023 | 88.75 ± 3.99 | 10.70 ± 0.16 |
| 7 | 4.0 | 0.025 | 0.6 | 547.33 ± 20.09 | 0.511 ± 0.024 | 92.79 ± 1.76 | 28.87 ± 1.39 |
| 8 | 2.5 | 0.01 | 0.2 | 163.13 ± 3.29 | 0.391 ± 0.053 | 87.94 ± 2.04 | −8.14 ± 0.51 |
| 9 | 1.0 | 0.025 | 0.6 | 535.33 ± 43.12 | 0.543 ± 0.053 | 93.22 ± 1.24 | 27.23 ± 0.31 |
| 10 | 1.0 | 0.025 | 0.2 | 132.77 ± 4.46 | 0.439 ± 0.061 | 87.61 ± 2.07 | −10.07 ± 1.26 |
| 11 | 1.0 | 0.04 | 0.4 | 219.53 ± 6.36 | 0.354 ± 0.071 | 90.63 ± 2.15 | 13.15 ± 0.75 |
| 12 | 4.0 | 0.025 | 0.2 | 132.97 ± 2.11 | 0.318 ± 0.022 | 84.78 ± 3.09 | −6.92 ± 0.16 |
| 13 | 2.5 | 0.025 | 0.4 | 255.83 ± 8.37 | 0.394 ± 0.128 | 85.44 ± 2.21 | 11.26 ± 2.04 |
| 14 | 2.5 | 0.025 | 0.4 | 252.30 ± 3.84 | 0.318 ± 0.088 | 86.38 ± 3.03 | 11.83 ± 2.67 |
| 15 | 2.5 | 0.025 | 0.4 | 259.77 ± 3.69 | 0.382 ± 0.043 | 85.15 ± 4.07 | 14.87 ± 1.89 |

Abbreviations:
$X_1$, Drug to phospholipid;
$X_2$, Surfactant concentration;
$X_3$, Coating solution concentration;
$Y_1$, Particle size (nm);
$Y_2$, Entrapment efficiency (%);
$Y_3$, Zeta potential (mV);
MR, Molar ratio;
PDI, Poly dispersity index Preparation of RSV Flexible-Lipid Based NPs Lipid film hydration technique was used to prepare the NPs formulations according to the method previously reported in our previously published work but with some modifications. Briefly, 100 mg of RSV and the calculated amount of phospholipid, edge activator (TWEEN®80) and DCP (15% w/w of the total lipid) were dispersed in 100 mL methanol in a Buchi rotavapor evaporating flask. The mix- Dynamic light scattering with non-invasive backscatter optics was the technique utilized in the measurement.

Entrapment Efficiency (EE)

The obtained RSV loaded flexible lipid-based nanocarriers (liposomal NPs and chitoplexes) were centrifuged at 20000 rpm for 1 h at 4° C. using 3K30 Sigma Laboratory centrifuge (Ostrode, Germany) to separate the free unentrapped drug. The supernatant was filtered through 0.2 μm Millipore filter and the drug concentration was estimated spectrophotometrically at 242 nm using 6705 UV/Vis spectrophotometer, Jenway (Stone, UK). The EE (%) for each formulation was calculated indirectly using the following equation.

$$EE(\%) = \frac{\text{Total amount of drug used} - \text{Calculated amount of free drug}}{\text{Total amount of drug used}} \times 100$$

Accuracy of the spectrophotometric method and its freedom from any possible interference by the formulation components were verified. Recovery testing for RSV concentration in different drug solutions containing the studied excipients was verified.

Box-Behnken Experimental Design Statistical Analysis

Data obtained for particle size, EE and zeta potential for the prepared flexible chitoplexes nano-formulations were statistically analyzed to identify the main, interaction and quadratic effects significantly affecting each response. The effect was considered significant at p-value less than 0.05.

Preparation and Characterization of the Formulation

The NP formulation was prepared and characterized for size, PDI, EE and zeta potential as described above. The observed values were compared to the predicted ones and the residual was calculated.

Morphological Study

A few drops of the chitoplexes nano-formulation were mounted on a carbon coated grid and left for 5 min to allow better adsorption of the NPs on the carbon film. Excess liquid was removed by a filter paper. Few drops of 1% phosphotungstic acid was added and the sample was examined using transmission electron microscopy (TEM), Model JEM-1230, JOEL (Tokyo, Japan). Morphology of the corresponding liposomal NPs formulation was also studied and compared to the chitoplexes nano-formulation.

Fourier Transforms Infrared (FT-IR)

The FT-IR spectra of pure RSV, phospholipid and chitosan samples were studied using a Nicolet Is10 of Thermo Scientific, Inc., (Waltham, Mass.). The spectra of the prepared liposomal NPs and chitoplexes nano-formulation were also investigated to identify any possible changes in the drug physicochemical characteristics following development of the flexible lipid-based NPs formulations. The FT-IR spectra of all the studied samples were recorded in the range of 4000-400 $Cm^{-1}$.

In Vitro Release Study

The in vitro release of RSV from the prepared liposomal NPs, chitoplexes nano-formulation and pure drug suspension was studied. A quantity of each preparation containing 9 mg of drug was placed in a firmly sealed dialysis bag (Sigma-Aldrich Inc.) of a molecular weight cut-off 14 kDa. The dialysis bag was immersed in a glass bottle containing 400 mL phosphate buffer of pH 7.4. The bottles were kept in a shaking water bath (Model 1031; GFL Corporation, Burgwedel, Germany) at 37° C. and 100 rpm. The parameters of the in vitro release study were selected to achieve a sink condition. Aliquots of 2 mL were taken from the receptor compartment at predetermined time intervals with immediate replacement. The quantity of RSV in the withdrawn samples was determined spectrophotometrically at 242 nm. The experiment was done in triplicate for each formulation and mean values were calculated.

Nanoparticle Flexibility

To evaluate the flexibility of the prepared NPs, the extrusion method was used. Concisely, the optimized chitoplexes nano-formulation and the corresponding liposomal NPs were separately extruded through a 0.1 mm pore size membrane filter under reduced pressure. The size of both NPs was measured before and after the extrusion process. The flexibility was estimated as the percent change in the NPs size according to the following equation:

$$\text{Flexibility} = \frac{\text{Size of the NPs before extrusion} - \text{Size of the NPs after extrusion}}{\text{Size of the NPs before extrusion}} \times 100$$

Cell Viability and Cytotoxicity Assay

This test aimed to determine the effect of the prepared RSV lipid-based NPs formulations on intestinal cell viability and cytotoxicity. The potential effects of both formulations on human colorectal (HCT-116) cells were assessed by 3-(4,5-dimethylthiazol-2-yl)2,5-diphenyl tetrazolium bromide (MTT) assay. Cells were seeded on 96-well plates ($1 \times 10^4$ cells/well) and incubated at 37° C. under a humidified atmosphere of 5% $CO_2$ for 24 h. The cell medium was then changed to serum free medium (SFM) alone or SFM containing pure RSV, RVS loaded liposomal NPs or RSV chitoplexes nano-formulation at different RSV concentrations (1.95, 3.91, 7.81, 15.63, 31.21, 62.5, 125, and 250 μM) and incubated for 72 h at 37° C. Each formulation was compared with a drug-free carrier as a negative control. After incubation, SFM in the control and test wells were replaced by 100 μL/well of MTT solution (0.5 mg/ml) in PBS and incubated at 37° C. for another 3 h. The MTT solution was removed and the purple formazan crystals formed at the bottom of the wells were dissolved using 100 μL DMSO/well with shaking for 2 h at room temperature. The intensity of the color obtained was measured at 549 nm using a microplate reader (ELX 800; Bio-Tek Instruments, Winooski, Vt., USA). Data, expressed as the percentage of viable cells, were compared to the survival of a control group. Values of the half maximal inhibitory concentration ($IC_{50}$) were also estimated. Cells treated with DMSO only were defined as 100%

Results

A great number of pharmacologically active compounds do not reach the commercialization step simply because of their limited oral bioavailability that is attributed to inadequate dissolution rate. A substantial problem that is currently confronting the pharmaceutical industry for drugs of limited aqueous solubility is mainly attributed to their limited dissolution rate. Also, during the first-pass metabolism phenomenon, a fraction of drug administered is lost during the absorption process due to the liver and/or gut wall metabolism. Accordingly, the drug concentration is greatly reduced before reaching the systemic circulation.

Chitosan-based NPs have been successfully developed and reported to have wide applications especially in oral drug delivery[22-25]. The reported benefits include: enhancing transport of active pharmaceutical ingredients across the intestinal epithelial cell layer, protection of insulin against degradation in the gastrointestinal fluid, enhancement of bioavailability and improvement of aqueous drug solubility. In this study, flexible liposomal NPs and their corresponding chitoplexes nano-formulation loaded with RSV were prepared to develop new nanocarrier systems suitable to investigate their role in intestinal cells cytotoxicity and improving RSV bioavailability.

Characterization of the Flexible Lipid-Based NPs Formulations

Flexible liposomal NPs were prepared using the lipid film hydration technique utilizing L-α phosphatidylcholine, dicetyl phosphate and TWEEN 80® as the main component of the liposomal membrane, negative charge inducing agent and edge activator, respectively. These flexible liposomal NPs were subsequently coated with chitosan to produce chitosan-coated flexible liposomes that have been assigned the name chitoplexes. Both NP formulations have been characterized for size, PDI, EE and zeta potential. Results for these parameters are given in Table 1. The diameter size of the obtained chitoplexes nano-formulation was in the range of 112.19±2.90-554.33±11.06 nm, the PDI was between 0.258±0.023-0.581±0.051, the EE was ranged between 84.78±3.09-94.59±1.62% and the obtained zeta potential value, which indicates surface charge of the particles, was in the range of (−10.07±1.26)-(+28.87±1.39) mV. Characterization of the corresponding flexible liposomal NPs revealed a vesicle size between 96.73±2.45-282.33±10.22 nm, PDI values in the range 0.3213±0.0290-0.5423±0.0236, an EE between 71.44±2.48-79.57±1.27% and negative zeta potential values of (−8.84±0.66)-(−12.73±0.81).

Experimental Design Statistical Analysis Results

Statistical analysis for the effect of the independent factors ($X_1$, $X_2$ and $X_3$) on the dependent responses ($Y_1$, $Y_2$ and $Y_3$) was accomplished by multiple regression analysis and two-way analysis of variance (ANOVA) using the StatGraphics software. Regression analysis is a statistical process that estimates and analyzes the relationships between a dependent variable and one or more of the independent variables. The two-way ANOVA aims to assess the main, interaction and quadratic effect of the independent variable on one dependent response. Accordingly, estimated effect of factors, F-ratios, and associated P-values were calculated and the obtained data are presented in Table 2. The sign of the estimated effect is an indication of a synergistic (positive sign) or antagonistic (negative sign) effect of this factor on the studied response. F-ratio is used to compare between the observed and expected averages. An F-ratio greater than 1 specifies a location effect and hence the P-value is used to report the significant level. If the obtained results for the P-value, for an independent factor, differs from zero and is less than 0.05, this factor is significantly affecting the studied response.

Effect of the Drug to Phospholipid Molar Ratio ($X_1$) on the Studied Responses ($Y_1$-$Y_3$)

Results of the statistical analysis, shown in Table 2, indicated that the drug to phospholipid molar ratio ($X_1$) significantly affected the particle size ($Y_1$,) at P-values of 0.0492. The pareto chart, displayed in FIG. 1, also confirmed this finding. A reference line is displayed in that chart. Any bar that extends after the line confirms a significant effect of a factor on the studied response. As indicated from the sign of the estimated effect and the pareto chart, $X_1$ exhibited an agonistic effect on $Y_1$.

Effect of the Surfactant Concentration ($X_2$) on the Studied Responses ($Y_1$-$Y_3$)

The surfactant concentration ($X_2$) significantly affected the particle size ($Y_1$,) and the EE ($Y_2$) at P-values of 0.0026 and 0.0431, respectively, as indicated by the pareto chart (FIG. 1) and the values of the estimated factors effects. $X_2$ antagonistically affected $Y_1$ and $Y_2$. Hence, increasing the surfactant concentration decreased the particle size and the EE of the prepared NPs. Effect of the chitosan solution concentration ($X_3$) on the studied responses ($Y_1$-$Y_3$)

It was noted that the concentration of the chitosan solution ($X_3$) significantly affected all the studied responses ($Y_1$-$Y_3$). This factor exhibited a synergistic, positive, effect on $Y_1$, $Y_2$ and $Y_3$. Bars in the pareto chart, FIG. 1, confirmed this finding. It was noted based on the ANOVA that the interaction effect of $X_3X_3$ significantly affected all the studied variables. $X_1X_1$, and $X_2X_2$ significantly affected $Y_2$, while $X_1X_2$ affected $Y_1$.

A mathematical model for the studied responses was generated and the polynomial equations that best fit the models are:

$$Y_1 = 167.497 + 25.282X_1 + 1236.66X_2 - 735.615X_3 - 1.82426X_1^2 - 557.556X_1X_2 + 9.83333X_1X_3 - 30853.7X_2^2 + 334.167X_2X_3 + 2130.95X_3^2$$

$$Y_2 = 102.625 - 4.82704X_1 - 464.259X_2 - 33.9708X_3 + 0.740741X_1^2 - 17.3333X_1X_2 + 2.0X_1X_3 + 8785.19X_2^2 + 15.0X_2X_3 + 56.9167X_3^2$$

$$Y_3 = -36.8913 - 0.841852X_1 - 61.1574X_2 + 160.79X_3 + 0.0148148X_1^2 + 76.7778X_1X_2 - 1.25833X_1X_3 + 4292.59X_2^2 - 581.667X_2X_3 - 72.7292X_3^2$$

TABLE 2

Estimated effects of factors, F-ratios, and associated P-values for the studied responses $Y_1$-$Y_3$

| | $Y_1$ | | | $Y_2$ | | | $Y_3$ | | |
|---|---|---|---|---|---|---|---|---|---|
| Factor | Estimated effect | F-ratio | P-Value | Estimated effect | F-ratio | P-Value | Estimated effect | F-ratio | P-Value |
| $X_1$ | 21.415 | 6.68 | 0.0492* | −1.67 | 6.08 | 0.0569 | 1.568 | 0.75 | 0.4262 |
| $X_2$ | −45.985 | 30.80 | 0.0026* | −1.825 | 7.26 | 0.0431* | 1.638 | 0.82 | 0.4073 |
| $X_3$ | 714.135 | 2252.15 | 0.00001* | 14.160 | 132.45 | 0.0001* | 35.187 | 114.48 | 0.0001* |
| $X_1X_1$ | −8.209 | 0.68 | 0.4472 | 3.333 | 16.76 | 0.0094* | 0.067 | 0.00 | 0.9767 |
| $X_1X_2$ | −25.09 | 6.88 | 0.0470* | −0.78 | 0.99 | 0.3645 | 3.455 | 2.73 | 0.1593 |
| $X_1X_3$ | 7.375 | 0.38 | 0.5644 | 1.5 | 2.35 | 0.1856 | −0.944 | 0.13 | 0.7328 |

TABLE 2-continued

Estimated effects of factors, F-ratios, and associated P-values for the studied responses $Y_1$-$Y_3$

| Factor | $Y_1$ | | | $Y_2$ | | | $Y_3$ | | |
|---|---|---|---|---|---|---|---|---|---|
| | Estimated effect | F-ratio | P-Value | Estimated effect | F-ratio | P-Value | Estimated effect | F-ratio | P-Value |
| $X_2X_2$ | −13.884 | 1.94 | 0.2220 | 3.953 | 23.58 | 0.0047* | 1.932 | 0.79 | 0.4154 |
| $X_2X_3$ | 2.506 | 0.04 | 0.8423 | 0.113 | 0.01 | 0.9129 | −4.363 | 2.79 | 0.1559 |
| $X_3X_3$ | 266.368 | 293.08 | 0.00001* | 7.115 | 31.27 | 0.0025* | −9.092 | 7.15 | 0.0442* |
| $R^2$ (%) | | 99.87 | | | 97.99 | | | 99.09 | |
| Adj. $R^2$ (%) | | 99.64 | | | 94.38 | | | 97.47 | |
| SE of Est. | | 9.57 | | | 0.782 | | | 2.091 | |
| Mean AE | | 4.82 | | | 0.406 | | | 1.058 | |

Abbreviations:
$X_1$, Drug to phospholipid;
$X_2$, Surfactant concentration;
$X_3$, Coating solution concentration;
$Y_1$, Particle size (nm);
$Y_2$, Entrapment efficiency (%);
$Y_3$, Zeta potential (mV);
$X_1X_2$, $X_1X_3$, and $X_2X_3$ are the interaction effects of the studied factors;
$X_1X_1$, $X_2X_2$ and $X_3X_3$ are the quadratic effects of factors;
SE, Standard error;
AE, Absolute error
Note:
*indicates significant effect of this factor on the studied response.

FIG. 1 also illustrates the three-dimensional estimated response surface plots that demonstrate the effect of two independent factors on a studied response when the value of the third factor was kept at an intermediate level. Individual analysis for the effect of the studied variables on the $Y_1$ indicated that to prepare flexible chitoplexes nano-formulation of 99.12 nm, the levels for $X_1$, $X_2$ and $X_3$ should be 1.0, 0.04 and 0.2, respectively as illustrated in Table 3. To obtain vesicles of 95.99% EE, the levels for $X_1$, $X_2$ and $X_3$ should be 1.0, 0.01 and 0.6, respectively. Flexible chitoplexes nano-formulation with a zeta potential value of 28.85 mV could be obtained at 1.0, 0.01 and 0.59 of $X_1$, $X_2$ and $X_3$, respectively. After analyzing the multiple effects of the studied variables on $Y_1$, $Y_2$ and $Y_3$, it was assumed that the smallest particle size, highest EE and highest zeta potential values could be achieved at $X_1$, $X_2$ and $X_3$ levels of 1.0, 0.01 and 0.47, respectively. A chitoplexes nano-formulation that contains these values was prepared, characterized and the values for predicted and observed values and their residuals are depicted in Table 3. The corresponding flexible liposomal NPs showed an average size of 230.34±8.73 nm, PDI value of 0.508±0.075, zeta potential value of −10.29±0.46 mV and EE of 78.13±0.54%.

TABLE 3

The optimum levels and values, and desirability levels and values for the studied factors and responses

| | | | Desired level for each response | | | |
|---|---|---|---|---|---|---|
| Factors | Low | High | $Y_1$ = 99.12 nm | $Y_2$ = 95.99% | $Y_3$ = 28.85 mV | Desired level |
| $X_1$ (MR) | 1.0 | 4.0 | 1.0 | 1.0 | 1.0 | 1.0 |
| $X_2$ (%) | 0.01 | 0.04 | 0.04 | 0.01 | 0.01 | 0.01 |
| $X_3$ (%) | 0.2 | 0.6 | 0.2 | 0.6 | 0.59 | 0.47 |

TABLE 3-continued

The optimum levels and values, and desirability levels and values for the studied factors and responses

| | | Desirability | | |
|---|---|---|---|---|
| Responses | Goal | Predicted values | Observed values | Residual |
| $Y_1$ (nm) | Minimize | 331.09 | 342.33 | 11.24 |
| $Y_2$ (%) | Maximize | 92.31 | 94.01 | 1.7 |
| $Y_3$ (mV) | Maximize | 19.39 | 21.22 | 1.83 |

Figure 2A:
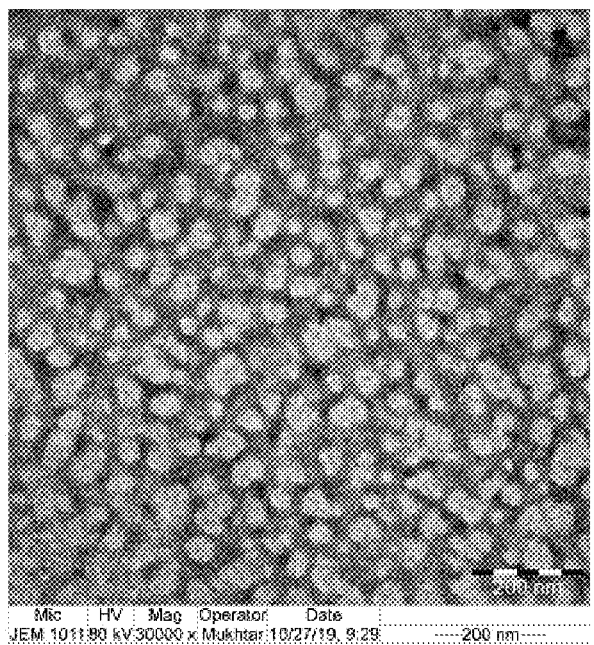
FIGS. 2A and B. Transmission electron microscope images of rosuvastatin liposomal nanoparticles (A); and chitoplexes nano-formulation (B).
Figure 2B:
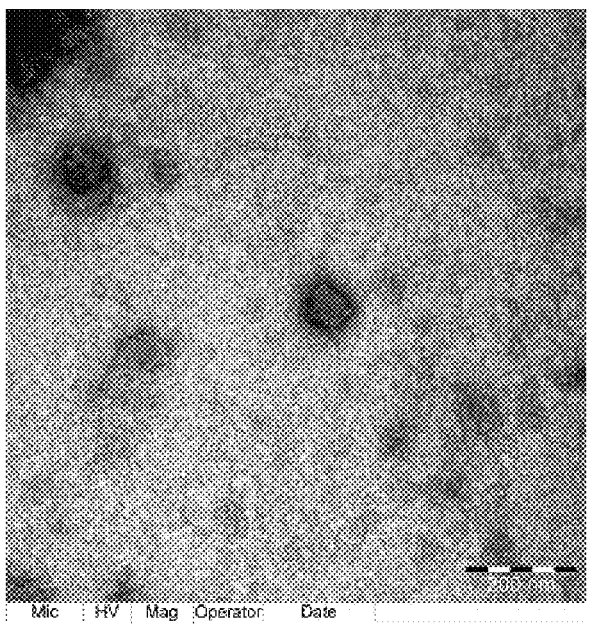

Abbreviations:
$X_1$, Drug to phospholipid;
$X_2$, Surfactant concentration;
$X_3$, Coating solution concentration;
$Y_1$, Particle size;
$Y_2$, Entrapment efficiency;
$Y_3$, Zeta potential;
MR, Molar ratio Morphological Characterization The vesicular nature of the liposomal NPs and chitoplexes nano-formulation was confirmed after investigation of their morphological characteristics as depicted in FIG. 2. Both formulations showed spherical shaped particles with a marked outer shell for chitoplexes nano-formulation. Addition of chitosan during preparation of the lipid-based vesicles resulted in deposition of this cationic polymer on the particles' outer surface, the effect that lead to formation of thick outer membrane. Moreover, chitoplexes nano-formulation exhibited a larger size compared to the corresponding liposomal NPs which is in good agreement with the results obtained from the particle size analysis.

Fourier Transforms Infrared (FT-IR)

The FT-IR spectrum for RSV loaded into different lipid-based nano-dispersed formulation without drying was studied. We aimed to identify the drug physicochemical changes in the developed liposomal NPs and chitoplexes nano-formulation without any further modifications in the formulation nature.

Figure 3:
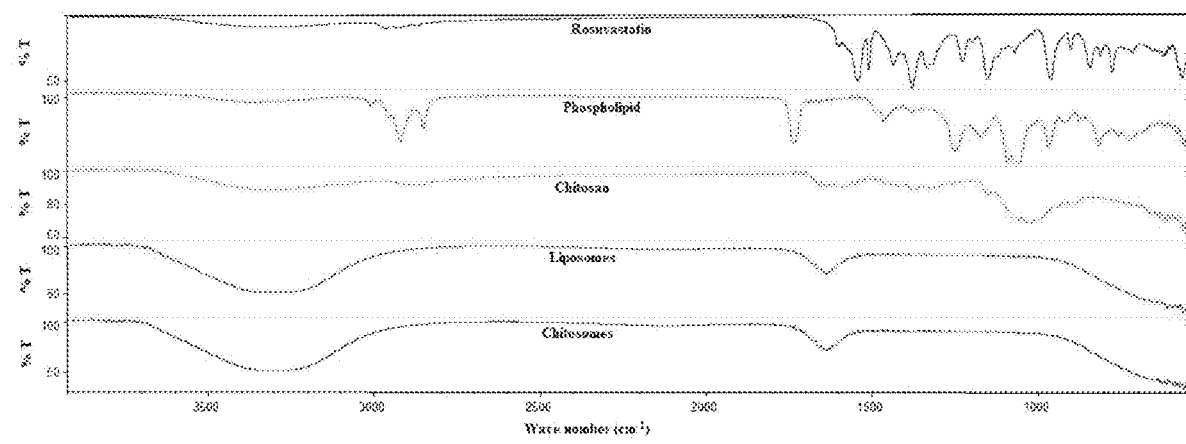
FIG. 3. Fourier-transformed infrared spectra of rosuvastatin, phospholipid, chitosan, liposomes nanoparticles and chitoplexes nano-formulation.

The FT-IR spectrum of pure RSV (FIG. 3) showed a broad band for O—H stretching at 3380 cm$^{-1}$ and a band at 2920

$cm^{-1}$ for =C—H stretching. Another two drug peaks were detected at 1550 $cm^{-1}$ and 1515 $cm^{-1}$ corresponding to C=C stretching and N—H bending, respectively. Asymmetric and symmetric bending vibration of the drug $CH_3$ group were noted at 1485 $cm^{-1}$ and 1380 $cm^{-1}$, respectively. The asymmetric vibration of S=O was observed at 1330 $cm^1$. The bending vibrations for C—H and C—F stretching were identified at 1230 $cm^{-1}$ and 1155 $cm^{-1}$, respectively.

The spectrum of the L-α phosphatidylcholine showed a broad peak at 3354 $cm^{-1}$ corresponding to the stretching vibration of the hydroxyl (OH) group. A sharp characteristic band between 2700 and 2950 $cm^{-1}$ originated from the C—H stretching vibration of the aliphatic methyl group. Another peak at 1735 $cm^{-1}$ assigned to C=O stretching was also detected. $PO_2$ antisymmetric double bond stretching bands were observed at 1250 $cm^{-1}$. Chitosan showed a broad band in the range of 3300-2900 $cm^{-1}$ corresponding to the amine and hydroxyl groups. A peak at 2876 $cm^{-1}$ that is attributed to —OH stretching; a characteristic band of the carbonyl (C=O) stretching of the secondary amide was detected at 1655 $cm^{-1}$, and the bending vibrations of the N—H (N-acetylated residues, amide II band) were observed at 1599 $cm^{-1}$.[26] Other peaks at 1423 and 1381 $cm^{-1}$ that belong to the N—H stretch of the amide and ether, respectively were also detected.

The spectrum of the liposomal NPs and chitoplexes nano-formulation confirmed the physical interaction between the studied components and effective encapsulation of RSV in the prepared nanovesicles. Broadening, overlapping, weak and/or disappearance of some bands in the spectra of the NPs formulation were noted. These changes were observed for phospholipid bands between 2700 and 2950 $cm^{-1}$, and at 1735 $cm^{-1}$; for drug peaks at 1515 and 1330 $cm^1$; and for chitosan peaks at 1599, 1423 and 1381 $cm^{-1}$. Phosphatidyl choline is a neutral or zwitterionic substance over a wide pH range from strongly acid to strongly alkaline.

In Vitro Release Study

Figure 4:
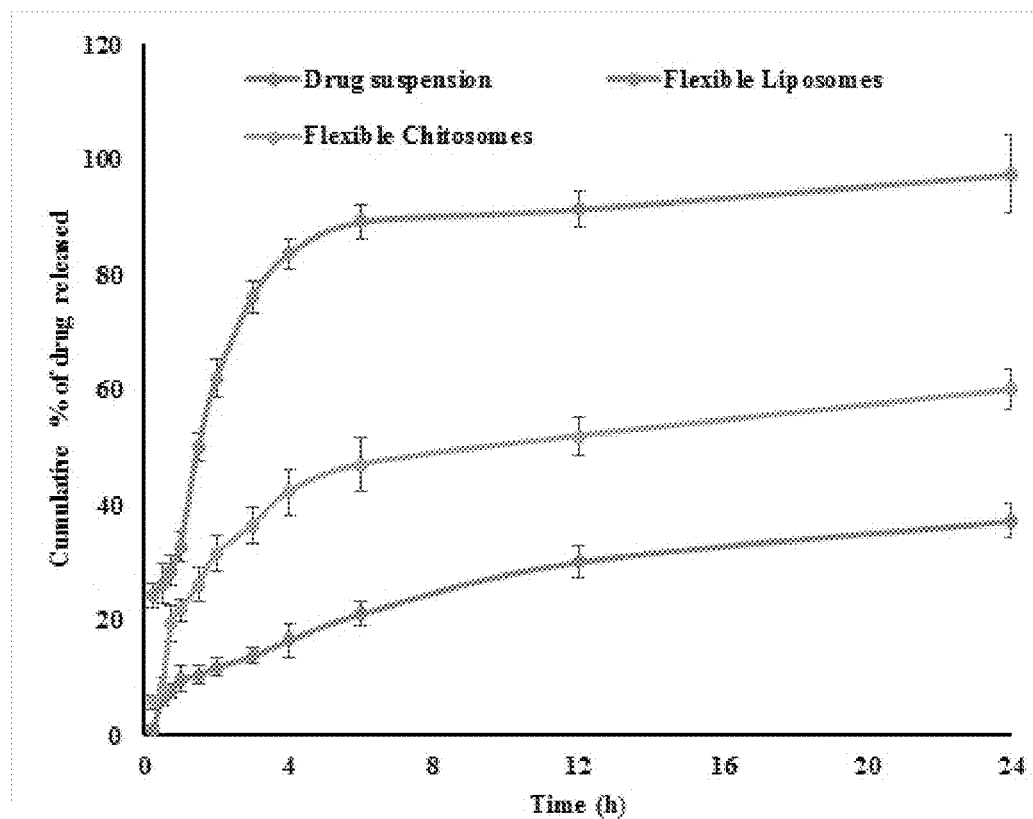
FIG. 4. In vitro release of rosuvastatin from a pure drug suspension, liposomes nanoparticles and chitoplexes nano-formulation.

The in vitro release of RSV from the prepared liposomal NPs and chitoplexes nano-formulation was studied and compared to that of a pure drug suspension using the dialysis bag technique. As depicted in FIG. 4, the release of RSV from the liposomal NPs illustrated a biphasic drug release pattern. An initial rapid drug release rate that was followed by a slow drug release pattern. The optimized flexible chitoplexes nano-formulation exhibited a lower initial drug release, compared to the corresponding liposomal NPs, the effect that is explained by the high EE (chitoplexes nano-formulation EE=94.01%). A second sustained release stage was observed for both liposomal NPs and chitoplexes nano-formulation. Drug suspension demonstrated an overall low drug release pattern, when compared to lipid-based NPs formulations, and smaller cumulative drug release due to the presence of the suspended drug particles in a coarse dispersion state.

NPs Flexibility

The ability of the prepared nanovesicles to pass through a 0.1 mm pore size membrane filter under reduced pressure was considered as a measurement of NPs flexibility. The prepared liposomal NPs and chitoplexes nano-formulation revealed a flexibility value of 44.43 and 40.16%, respectively.

Cell Viability and Cytotoxicity Assay

Statins possess anticancer activity against many cancer cells under in vitro conditions in a time- and dose-dependent manner Previous studies have shown that RSV demonstrated a cytotoxic activity against thyroid, hepatic, breast, cervical and prostate cancer cell lines. Another study illustrated the anti-melanoma properties of RSV. The anticancer activity of statins is attributed to their ability to inhibit the mevalonate pathway, which leads to reduction of cholesterol synthesis, and to their ability to decrease the cellular levels of non-steroidal isoprenoids, geranylgeranyl pyrophosphate and farnesyl pyrophosphate. These effects result in failure of protein prenylation which affects carcinogenesis. As far as we know, RSV activity against intestinal cells had not been studied prior to the present work.

Figure 5A:
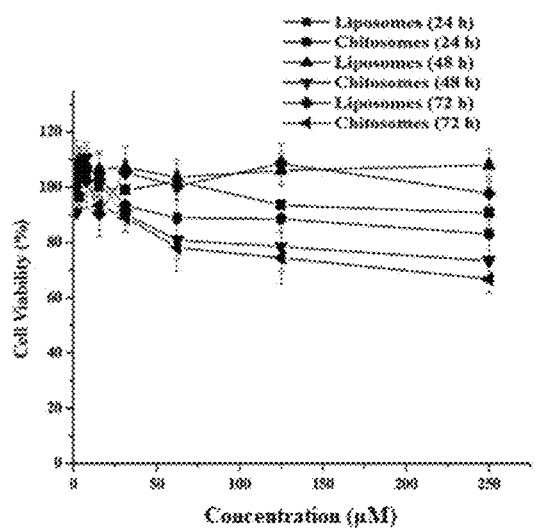
FIGS. 5A and B. Cell viability after treatment with free liposome nanoparticles and chitoplexes nano-formulation (A); and following treatment with rosuvastatin loaded liposome nanoparticles and chitoplexes nano-formulation (B).
Figure 5B:
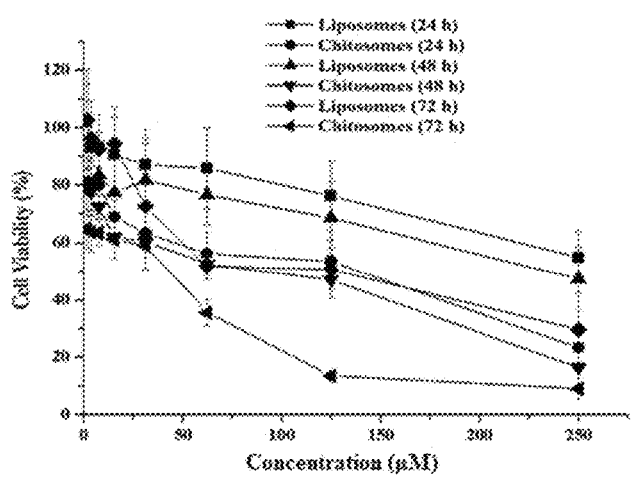

To examine the biocompatibility and cytotoxic effects of plain and drug loaded liposomal NPs or chitoplexes nano-formulation, HCT-116 cells were treated with different concentrations of these samples for 3 days and the MTT assay was performed to investigate the effect of these formulation on the viability of living cells. This test depends on the production of a colored formazan by the action of the viable cells' mitochondrial enzymes on MTT. Cells were exposed to increasing RSV concentrations of drug loaded liposomal NPs and chitoplexes nano-formulation standardized at certain RSV concentrations. Cells were also incubated with blank liposomal NPs and chitoplexes nano-formulation to exclude the effect of RSV. As shown in FIG. 5, cellular proliferation was inhibited in a dose-dependent manner of RVS. The inhibition difference between plain (drug free) chitoplexes and liposomes treated with 250 μM at 24 h was much less than its drug-loaded counterpart, the effect that could be attributed to the prominent drug cytotoxic effect at this concentration.

Interestingly, the $IC_{50}$ values of chitoplexes nano-formulation were found to be smaller than the corresponding liposomal NPs as shown in Table 4. The calculated $IC_{50}$ values for chitoplexes nano-formulation were about 142.5, 98.6 and 43.9 μM after 24, 48 and 72 h respectively, while that of liposomal NPs were 234.8, 218.8 and 131.7 μM respectively, after the same amounts of time.

TABLE 4

The calculated half maximal inhibitory concentration following treatment with different rosuvastatin formulations

| Formulation | $IC_{50}$ (μM) | | |
| --- | --- | --- | --- |
| | after 24 h | after 48 h | after 72 h |
| RSV Chitoplexes | 142.5 | 98.6 | 43.9 |
| RSV Liposomes | 234.8 | 218.8 | 131.7 |
| RSV pure | 247.5 | 236.8 | 168.5 |

Discussion

As the drug to phospholipid molar ratio was increased from 1:1 to 1:4, the particle size of the prepared NPs increased. At higher phospholipid loads, the formation of multilamellar vesicles is favored, the effect that results in increasing the size of the prepared NPs.

The effect of the surfactant concentration on particle size could be attributed to the reduction of the surface tension of the media at higher surfactant concentration resulting in the arrangement of the phospholipid in small vesicles. The decrease in the EE of the prepared vesicles that was observed at higher surfactant concentrations could be attributed to the formation of micelle molecules that compete for the drug molecules with the lipid vesicles.

The particle size, EE and zeta potential of the drug loaded NPs increased as the concentration of chitosan (coating) solution was increased. Addition of chitosan to the flexible liposomal vesicles resulted in coating of the NPs outer surface by an electrostatic interaction between the positively charged chitosan and the negatively charged NP surface. This coating process resulted in an enlargement of the vesicles. Deposition of more chitosan on the NPs surface was achieved at higher polymeric concentration, an effect that results in increasing the zeta potential value and promotion of more drug entrapment in the coated NPs. The electrostatic interaction between the negatively charged drug and the positively charged chitosan, that deposited on the NPs surface, may be another cause for the increase in drug EE at higher chitosan concentrations.

Encapsulation of RSV in the phospholipid molecules, adsorption of the DCP at the phospholipid molecules and chitosan coating of the flexible liposomal NPs may result in electrostatic interaction by weak van der Waals forces of attraction or dipole-dipole and hydrogen bond formation. This finding was confirmed after FTIR characterization.

The amount of drug that was released from the liposomal NPs during the early stage is mainly attributed to non-encapsulated drug (liposomal NPs EE=78.13±0.54%), drug adsorbed on the NPs surface and to drug permeated from the prepared NPs. Chitoplexes nano-formulation showed an extended drug release pattern due to the presence of chitosan in the outer shell which delayed the diffusion of RSV into the release medium. The second sustained release stage that was observed for both liposomal NPs and chitoplexes nano-formulation could be attributed to encapsulation of RSV within the lipid shell that allows slow drug release from the lipid matrix. After 24 h, the values for drug release from liposomal NPs, chitoplexes nano-formulation and pure drug suspension were 97.54±3.37, 59.98±3.47 and 37.28±2.86%, respectively.

The flexibility values of both formulations indicated the elasticity of the prepared NPs, an effect that is attributed to the presence of the edge activator component. The presence of the edge activator weakens the phospholipid bilayer and renders the nano-vesicle ultra-deformable. Chitoplexes nano-formulation demonstrated less flexibility than the corresponding liposomal NPs, an effect that is attributed to the chitosan coating process.

Cellular proliferation was inhibited in an RVS dose-dependent manner, as indicated in the reduction in cell viability upon increasing the drug concentration in the prepared liposomal NPs and chitoplexes nano-formulation. The smaller $IC_{50}$ values of chitoplexes nano-formulation when compared to the corresponding liposomal NPs indicate a gradual release of RSV from the NPs phospholipid bilayers and the significant effect of the chitosan layer on cell viability when compared to liposomal NPs. Positivity of the NPs outer shell demonstrated a marked cytotoxic effect which was also obvious with plain (drug free) chitoplexes nano-formulation but to a lesser extent. This finding indicates the higher therapeutic window of RSV chitoplexes nano-formulation. Accordingly, chitoplexes nano-formulation are excellent nanocarriers to effect RSV cytotoxic activity.

CONCLUSION

Chitoplexes nano-particles exhibited a spherical shape, a distinct outer shell membrane and a larger vesicles size when compared to corresponding liposomal NPs. Both formulations illustrated a biphasic drug release profile. Chitoplexes nano-formulation exhibited a lower initial and more extended drug release pattern when compared to liposomal NPs. Chitoplexes nano-formulation advantageously exhibited smaller $IC_{50}$ values and superior anticancer activity in a time- and dose-dependent manner, compared to corresponding liposomal NPs.

While the invention has been described in terms of its several exemplary embodiments, those skilled in the art will recognize that the invention can be practiced with modification within the spirit and scope of the appended claims. Accordingly, the present invention should not be limited to the embodiments as described above but should further include all modifications and equivalents thereof within the spirit and scope of the description provided herein.

FUNDING STATEMENT

This project was funded by the Deanship of Scientific Research (DSR), at King Abdulaziz University, Jeddah, under grant no. (RG-13-166-40). The authors, therefore, acknowledge with thanks DSR for technical and financial support.

We claim:

1. A flexible chitosan-coated formulation, comprising
an interior comprising
    at least one phospholipid,
    at least one edge activator,
    at least one charge inducing agent, and
    at least one statin, wherein the at least one statin is rosuvastatin, and
an exterior coating of chitosan that encapsulates the interior,
wherein
    the at least one phospholipid is present in an amount of from 1:1-1:4 statin to phospholipid molar ratio;
    the at least one edge activator is present in an amount of from 0.01-0.04% (w/v) based on the total formulation volume;
    the at least one charge inducing agent is present in an amount of 10 to 20% w/w of the total lipid;
    the at least one statin is present in an amount of 0.01 to about 0.5% (w/v), and
    the chitosan is present in an amount of 0.4-0.6% (w/v) to provide an entrapment efficiency of at least 80%, a zeta potential of −15 to +30 millivolts, and an $IC_{50}$ of about 142.5 µM for cell viability at 24 hours after treatment of colorectal cancer cells,
wherein a diameter of the flexible chitosan-coated nanoparticle ranges from 100 to 600 nm.

2. The flexible chitosan-coated formulation of claim 1, wherein
    the at least one phospholipid is phosphatidylcholine;
    the at least one edge activator is polysorbate-80; and
    the at least one charge inducing agent is dicetyl phosphate.

3. A method of making a flexible chitosan-coated formulation, comprising
    preparing a liposomal interior comprising
        at least one phospholipid,
        at least one edge activator,
        at least one charge inducing agent, and
        rosuvastatin,
and
    coating the liposomal interior with an exterior coating of chitosan that encapsulates the interior,
wherein
    the at least one phospholipid is added in an amount of from 1:1-1:4 rosuvastatin to phospholipid molar ratio;

the at least one edge activator is added in an amount of from 0.01-0.04% (w/v) based on the total formulation volume;

the at least one charge inducing agent is added in an amount of 10 to 20% w/w of the total lipid;

the rosuvastatin is added in an amount of 0.01 to about 0.5% (w/v), and the chitosan is added in an amount of 0.4-0.6% (w/v) to provide an entrapment efficiency of at least 80%, a zeta potential of −15 to +30 millivolts, and an $IC_{50}$ of about 142.5 μM for cell viability at 24 hours after treatment of colorectal cancer cells, wherein a diameter of the flexible chitosan-coated nanoparticle ranges from 100 to 600 nm.

4. The method of claim 3, wherein the at least one phospholipid is selected from the group consisting of: phosphatidylcholine, phosphatidylethanolamine, phosphatidylserine, phosphatidic acid, phosphatidylinositol and phosphatidylglycerol.

5. The method of claim 3, wherein the at least one edge activator is selected from the group consisting of polysorbate-20, polysorbate-40, polysorbate-60, and polysorbate-80.

6. The method of claim 3, wherein the at least one charge inducing agent is selected from the group consisting of: dicetyl phosphate, phosphatidic acid, stearylamine and cetylpyridinium chloride.

7. The method of claim 3, wherein
the at least one phospholipid is phosphatidylcholine;
the at least one edge activator is polysorbate-80; and
the at least one charge inducing agent is dicetyl phosphate.

8. The method of claim 3, wherein the exterior coating of chitosan has a thickness ranging from 15.46 to 272.01 nm.

9. The method of claim 3, wherein the thickness of the exterior coating of chitosan is 100.75 nm.

* * * * *